(12) United States Patent
Parida

(10) Patent No.: US 7,203,680 B2
(45) Date of Patent: Apr. 10, 2007

(54) SYSTEM AND METHOD FOR ENCODING AND DETECTING EXTENSIBLE PATTERNS

(75) Inventor: Laxmi P. Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 481 days.

(21) Appl. No.: 10/677,016

(22) Filed: Oct. 1, 2003

(65) Prior Publication Data

US 2005/0076026 A1 Apr. 7, 2005

(51) Int. Cl.
*G06F 17/30* (2006.01)
*G06F 7/00* (2006.01)

(52) U.S. Cl. .......................................... 707/6; 707/100
(58) Field of Classification Search .................... 707/5, 707/6, 100–102; 702/19, 20; 382/129, 217; 706/48, 45–46, 55
See application file for complete search history.

(56) References Cited

U.S. PATENT DOCUMENTS

| | | | | |
|---|---|---|---|---|
| 5,570,306 A | * | 10/1996 | Soo | 708/212 |
| 5,577,249 A | * | 11/1996 | Califano | 707/100 |
| 5,701,256 A | * | 12/1997 | Marr et al. | 702/20 |
| 6,092,065 A | * | 7/2000 | Floratos et al. | 707/6 |
| 6,373,971 B1 | * | 4/2002 | Floratos et al. | 382/129 |
| 6,571,230 B1 | | 5/2003 | Parida | 706/48 |
| 6,584,465 B1 | * | 6/2003 | Zhu et al. | 707/6 |
| 6,785,672 B1 | * | 8/2004 | Floratos et al. | 707/3 |

OTHER PUBLICATIONS

Abhijit Chattaraj and Laxmi Parida, "An Inexact-Suffix Tree Based Algorithm for Detecting Extensible Patterns."

* cited by examiner

*Primary Examiner*—Greta Robinson
*Assistant Examiner*—Jacques Veillard
(74) *Attorney, Agent, or Firm*—Michael J. Buchenhorner

(57) ABSTRACT

Given an input sequence of data, a rigid pattern is a repeating sequence, possibly interspersed with don't-care characters. The data can be a sequence of characters or sets of characters or even real values. In practice, the patterns or motifs of interest are the ones that also allow a variable number of gaps (or don't-care characters): these are patterns with spacers termed extensible patterns. In a bioinformatics context, similar patterns have also been called flexible patterns or motifs. A system according to the invention discovers all the maximal extensible motifs in the input. The flexibility is succinctly defined by a single integer parameter $D \geq 1$ which is interpreted as the allowable space to be between 1 and D characters between two successive solid characters in a reported motif.

20 Claims, 12 Drawing Sheets

| Freq | Seq | Motif | Occurrences |
|---|---|---|---|
| 2 | 2 | DVHG.....GMLCAGFLEGGTD | (5:85-106); (8:0-21); |
| 2 | 2 | H-L..ML-F-A-D.....V.E | (1:72-105); (8:2-34); |
| 2 | 2 | F-E.S......V..I......P..H-F...ML-F-D | (1:45-97); (5:59-106); |
| 2 | 2 | F-E.S......V..I......P..H-F...T-ML-F-D | (1:45-97); (5:59-106); |
| 2 | 2 | H-S-ML-F-A-D.....V.E | (1:72-105); (8:2-34); |
| 2 | 2 | ML-F-D-S-E | 1:82-104); (8:10-34); |
| 3 | 3 | ML-F-D | (1:82-97); (5:95-106); (8:10-21); |
| 2 | 2 | C-L-R-T....T.S-MK-V-D......V | (1:3-58); (2:60-95); |
| 2 | 2 | RC-H-T..L-E-ME-E-L......L-Y......T-D-T | (0:42-105); (2:3-72); |
| 2 | 2 | E.......F...E.S..LQEA-I.P.RC-H-T-L-L-G-T | (0:10-62); (5:51-105); |
| 2 | 2 | L-Q......RC-P...G-LC...L-D | (4:66-101); (5:68-106); |
| 2 | 2 | G-S.LQ.....L-RC-P...G-LC...L-D | (4:66-101); (5:68-106); |
| 2 | 2 | K-K...S-N-L.....L-E-RC.......L-L | (0:2-53); (4:46-95); |
| 2 | 2 | E.......F.....E.S..LQE-P-RC-H-T-L-L-G-T | (0 :10-62) ; (5 :51-105) ; |
| 2 | 2 | RC...D......Q....C-E | (4:0-19); (5:80-102); |

*FIG. 15*

| Freq | Seq | Motif |
|---|---|---|
| 2 | 2 | [FYM [DNSR] .[DNSR]G [DNSR]PF S .A E C HYE [FYWI] AA T F T |
| 2 | 2 | [DNSR] .M F D DV EL [FYWI]N.PG YT.V L[DNSR]V |
| 2 | 2 | [DNSR]M F D DV[DNSR][DNSR] .IS PG YT.V L[DNSR]V |
| 2 | 2 | [DNSR]M F D D V [DNSR]L S PG YT.V L[DNSR]V |
| 2 | 2 | V S PG LETS[DNSR][DNSR] G[DNSR] D Y.D Y |
| 2 | 2 | [DNSR]M F D D V [DNSR]LI S PG YT.V L[DNSR]V |
| 2 | 2 | S PG C T .DV [DNSR] R[DNSR] T .[DNSR][DNSR] |
| 2 | 2 | S PG [FYWI) L E T S |
| 2 | 2 | S PG [FYWIJ ETS[DNSR][DNSR] G[DNSR] D Y.D Y |
| 2 | 2 | S PG [FYWTj D .GCR[DNSR] T[DNSR][DNSR] |
| 2 | 2 | S PG (FYWI] D G S .[DNSR][DNSR] G[DNSR] D Y.D Y |
| 2 | 2 | S PG [FYW~ D D G C .R[DNSR] T[DNSR][DNSR] |
| 2 | 2 | S PG [FYWI) D A .(FYWI) T PNSR] |
| 3 | 2 | S PG [FYWI] D |
| 2 | 2 | A PI L L[DNSR] H |
| 2 | 2 | A STYA LA C[DNSR].[FYWI][DNSR]E CA Q S VPLQ A |

*FIG. 16*

[DNSR]....M-(4,6)F-(2,5)D-(4,6)D....V-(1,4)E........L-(2,7)[FYWI].....N.PG-(1,2)YT.V-(1,3)L...[DNSR]...V

[DNSR]....M-(4,6)F-(2,5)D-(4,6)D....V......[DNSR][DNSR]...I..S-(5,7)PG- (1,2)YT.V-(1,3)L...[DNSR]...V

[DNSR].....M-(4,6)F-(2,5)D-(4,6)D-(5)V-(7)[DNSRJ...L-(6,7)S-(5,7)PG-
   (1,2)YT.V-(1,3)L...[DNSR]...V

V-(2,7)S-(3,5)PG-(1,4)L.....E..T.....S.....[DNSR]....[DNSR]-(1,5)G..[DNSR]-
   (1,6)D-(1,6)Y.D (1,2)Y

[DNSR].....M-(4,6)F-(2,5)D-(4,6)D-(5)V-(7)[DNSR]...L..I-(3,4)S-(5,7)PG-(1,2)YT.V-(1,3)0L...[DNSR]...V

S-(3,5)PG-(1,2)C-(1,7)T.....D....V-(2,4)[DNSR]-(4,7)R[DNSR]-(1,4)T
....[DNSR]...[DNSR]

S-(5,7)PG-(1,2)[FYWI]-(1,6)L (4,5)E-(1,2)T-(1,6)S

S-(3,5)PG-(2,5)[FYWI]-(1,7)E..T.....S.....[DNSR]...[DNSR]-(1,5)G..[DNSR]- (1,6)D-(1,6)Y.D (1,2)Y

S-(3,5)PG-(2,5)[FYWI]-(5,6)D-(1,4)D-(1,5)G-(3,4)C.....R[DNSR]-(1,4)T....[DNSR]...[DNSR]

S-(3,5)PG-(2,5)[FYWI]-(5,6)D-(3,7)G-(1,2)S.....[DNSR]...[DNSR]-
   1,5)G ...[DNSR]-(1,6)D-(1,6)Y.D (1,2)Y

S-(3,5)PG-(2,5)[FYWI]-(5,6)D-(1,4)D-(1,5)G-(3,4)C.....R[DNSR]-(1,4)T ....[DNSR]...[DNSR]

S-(3,5,7)PG-(1, 2,5) [FYWI]-(1,5,6)D

A-(2,6)PI....L-(1,2)L.......[DNSR]-(3,4)H

*FIG. 17*

SYSTEM AND METHOD FOR ENCODING AND DETECTING EXTENSIBLE PATTERNS

CROSS-REFERENCE TO RELATED APPLICATIONS

Not Applicable.

STATEMENT REGARDING FEDERALLY SPONSORED-RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The invention disclosed broadly relates to the field of information processing systems, and more particularly relates to the field of systems for detecting patterns in information strings.

BACKGROUND OF THE INVENTION

A rigid motif is a repeating pattern in a string of data comprising a plurality of tokens such as alphabet characters, possibly interspersed with don't-care characters that has the same length in every occurrence in the input sequence. Pattern or motif discovery in data is widely used for understanding large volumes of data such as DNA or protein sequences.

Allowing the motifs to have a variable number of gaps (or don't-care characters), called patterns with spacers or extensible motifs, further increases the expressibility of the motifs. For example, given a string s=abcdaXcdabbcd, m=a.cd is a rigid pattern that occurs twice in the data at positions 1 and 5 in s. In the above example, the extensible motif, where the number of don't-care characters between a and c of the pattern is one or two, would occur three times at positions 1, 5 and 9. At position 9 the dot character represents two gaps instead of one.

The task of discovering patterns must be clearly distinguished from that of matching a given pattern in a string of characters or database. In the latter situation, we know what we are looking for, while in the former we do not know what is being sought. Typically, the higher the self similarity (i.e., repeating patterns) in the sequence, the greater is the number of patterns or motifs in the data. Motif discovery on data such as repeating DNA or protein sequences is indeed a source of concern because these exhibit a very high degree of self similarity. The number of rigid maximal motifs could potentially be exponential in the size of the input sequence.

The problem of a large number of motifs is usually tackled by pre-processing the input, using heuristics, to remove the repeating or self similar portions of the input or using a statistical significance measure. However, due to the absence of a good understanding of the domain, there is no consensus over the right model to use. Thus there is a trend towards model-less motif discovery in different fields. There has been empirical evidence showing that the run time is linear in the output size for the rigid motifs and experimental comparisons between available implementations.

Consider an example of a rigid pattern (albeit with don't-care characters) discovery tool that is often inadequate in detecting biologically significant motifs. Fibronectin is a plasma protein that binds cell surfaces and various compounds including collagen, fibrin, heparin, DNA, and actin. The major part of the sequence of fibronectin consists of the repetition of three types of domains, which are called type I, II, and III. The type II domain is approximately forty residues long, contains four conserved cysteines involved in disulfide bonds and is part of the collagen binding region of fibronectin. In fibronectin the type II domain is duplicated. Type II domains have also been found in various other proteins. The fibronectin type II domain pattern has the following form:

C...PF.[FYWI].......C-(8,10)WC....[DNSR] [FYW]-(3,5)[FYW].[FYWI]C

The extensible part of the pattern is shown as integer intervals. It is clear that a rigid pattern discovery tool will never capture this as a single domain. Therefore, there is need for a system and method of pattern discovery that overcomes the drawbacks in the prior art.

SUMMARY OF THE INVENTION

Briefly, according to the invention an input string of tokens (e.g., characters) is analyzed for token patterns. A system embodying the invention is based on an inexact suffix tree construction which provides a framework for an output sensitive detection algorithm.

BRIEF DESCRIPTION OF THE DRAWINGS

FIGS. 15–16 are tables showing the results of using a method according to the invention on a collection of fibronectin sequences.

FIG. 17 is a small sample output after using the method according to the invention on a collection of fibronectin sequences.

DETAILED DESCRIPTION

Figure 1:
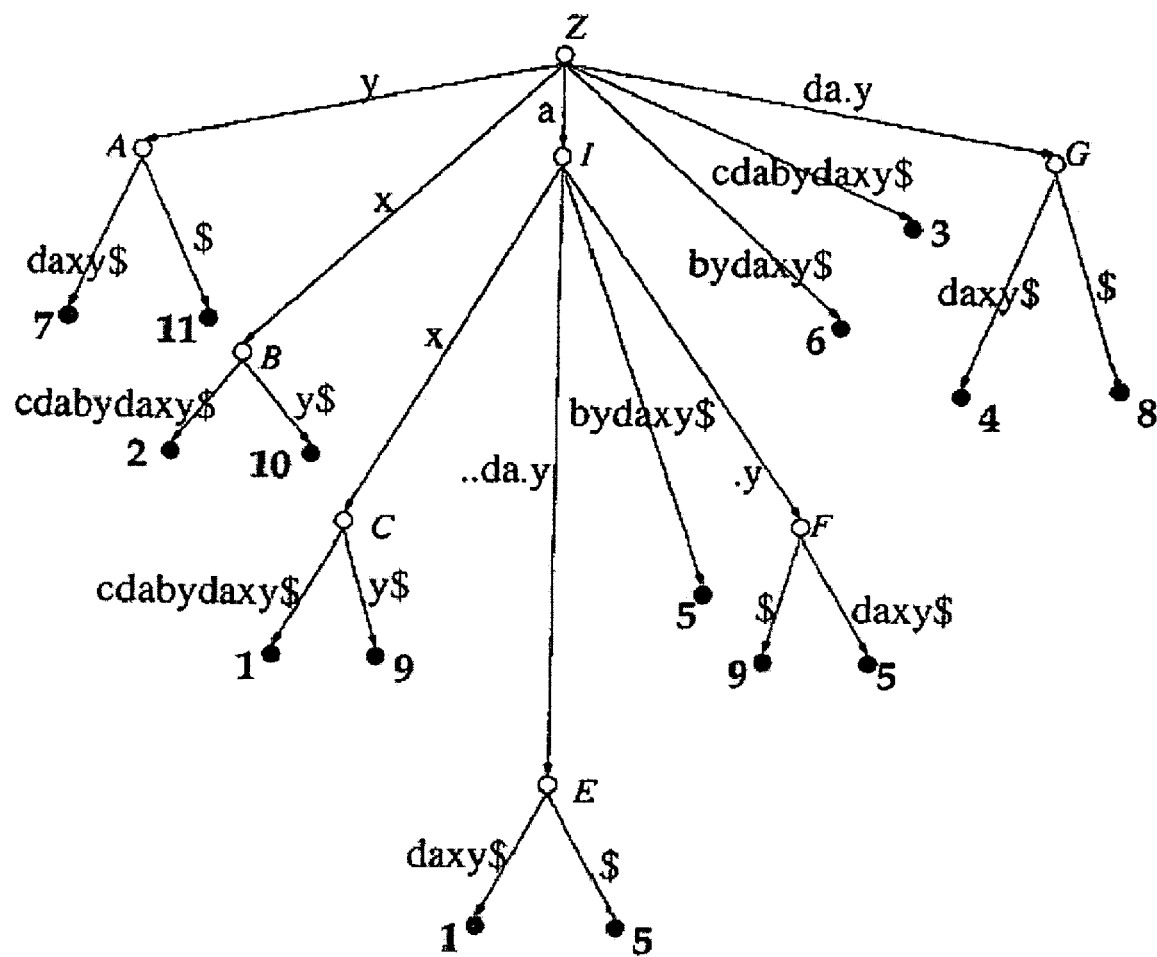
FIG. 1 shows an inexact suffix tree for a token string.

To facilitate a clear understanding of the present invention, definitions of terms employed herein will now be given.

Dot character: The '.' is called a "don't-care" or a dot character and any other element is called solid. Also, $\sigma$ will refer to a singleton character or a set of characters from $\Sigma$. Let s be a sequence of sets of characters from an alphabet $\Sigma$, '.'$\notin \Sigma$. For brevity of notation, a singleton set is not enclosed in curly braces. For example, let $\Sigma=\{A, C, G, T\}$, then $s_1$=ACTGAT and $s_2=\{A,T\}CG\{T, G\}$ are two possible sequences. The $j^{th}$ ($1 \leq j \leq |s|$) element of the sequence is given by s[j]. For instance in the above example $s_2[1]=\{A, T\}$, $s_2[2]=\{C\}$, $s_2[3]=\{G\}$ and $s_2(4)=\{T, G\}$. Also, if x is a sequence, then |x| denotes the length of the sequence and if x is a set of elements then |x| denotes the cardinality of the set. Hence $|s_1|=6$, $|s_2|=4$, $|s_1|[1]=1$ and $|s_2|[4]=2$.

$e_1 \preceq e_2$: We say that $e_1 \preceq e_2$ if and only if $e_1$ is a don't-care character or $e_1$ is a subset of $e_2$. For example, if $e_1=\{A, C\}$, $e_2=\{A,C,G\}$ and $e_3=\{T\}$ are three elements of some sequence, then $e_1 \preceq e_2$ and $e_1 \npreceq e_3$.

Annotated Dot Character, $.^\alpha$: An annotated "." character is written as $.^\alpha$ where $\alpha$ is a set of non-negative integers $\{\alpha_1, \alpha_2, \ldots, \alpha_3\}$ or an interval $\alpha=[\alpha_l, \alpha_u]$, representing all integers between $\alpha_l$ and $\alpha_u$ including $\alpha_l$, and $\alpha_u$. To avoid clutter, the annotation superscript $\alpha$ will be an integer interval.

Rigid, extensible string: Given a string m, if at least one dot element, is annotated, m is called a extensible string, otherwise m is called rigid.

Realization: Let m be a extensible string. A rigid string m' is a realization of m if each annotated dot element, $.^\alpha$ is replaced by l dot elements where $l \in \alpha$. For example, if $m=\alpha.[^{2,4}]b.[^{3,6}]cde$, then m'=a...b...cde is a realization of m and so is m"=a...b....cde.

m occurs at l: A rigid string m occurs at position l on s if $m[j] \preceq s[l+j]$ holds for $1 \leq j \leq |m|$. A extensible string m occurs at position l in s if there exists a realization m' of m that occurs at l. If m is extensible then m could possibly occur a multiple number of times at a location on a string s. For example, if s=axbcbc, then $m=a.[^{1,3}]b$ occurs twice at position 1 as axbcbc and axbcbc.

Size of m, |m|: If m is rigid, size of m is the number of solid and dot characters in m and is denoted by |m|. If m is extensible and occurs at positions in $L_m$, then $|m|=\max_i |m'_i|$ where $m'_i$ is a realization of m that occurs at $i \in L_m$. Consider s=abcdabeed. Let $m_1$=ab, $m_2$=ab-d. Then $|m_1|$=2 and $|m_2|=\max\{|ab.d|, |ab..d|\}=5$.

k-motif m, location list $L_m$: Given a string s on alphabet $\Sigma$ and a positive integer k, $k \leq |s|$, a string (extensible or rigid) m is a motif with location list $L_m=(l_1,l_2,\ldots,l_p)$, if $m[1] \neq$ '.', $m[|m|] \neq$ '.' and m occurs at each $l \in L_m$ with $p \geq k$. Also $L_m$ is complete, i.e., if there exists j such that m occurs at j then $j \in L_m$. To avoid clutter, in the rest of the discussion a k-motif will be referred to simply as a motif. The associated k should be clear from the context.

Realization of a motif m of s: Given a motif m on an input string s with a location list $L_m$, and m' a realization of the string m, then m' is a realization of the motif m if and only if there exists some $i \in L_m$ such that m' occurs at i in s.

Notice that because of our notation of annotating a dot character with an integer interval (instead of a set of integers), not every realization of the extensible string occurs in the input string. For example for s=axbcbc, $p=a.^{[1,3]}b$ is a extensible motif on s. p'=a..b is a realization of the string p but not of the motif p since p' does not occur in s. In the remaining discussion we will use this stricter definition of motif realization unless otherwise specified.

$m_1 \preceq m_2$: Given two motifs $m_1$ and $m_2$ on s $m_1 \preceq m_2$ holds if at each occurrence i on s, the realization $m'_1$ of motif $m_1$ at i there exists a realization $m'_2$ of motif $m_2$ at i such that $m'_1[j] \preceq m'_2[j]$, $1 \leq j \leq l$ where $l=\max |m'_1|, |m'_2|$. For example, let $m_1$=AB..E and $m_2$=ABC.E.G occurring at position 1 of string s=ABCXEYGXXABYYEABCYEYG. Then $m_1 \preceq m_2$ at position 1, and $m_2 \npreceq m_1$ at position 1.

Sub-motifs of motif m: Given a motif m let $m[j_1], m[j_2], \ldots m[j_l]$ be the l solid elements in the motif m. Then the sub-motifs of m are given as follows: for every $j_i$, $j_{i'}$ the sub-motif $m[j_i \ldots j_{i'}]$ is obtained by dropping all the elements before (to the left of) $j_i$ and all elements after (to the right of) $j_{i'}$ in m.

Maximal Motif: Let $m_1, m_2, \ldots, m_k$ be the motifs in a string s. A motif $m_i$ is maximal in composition if and only if there exists no $m_l$, $l \neq i$ with $L_{mi}=L_{ml}$, and $m_i \preceq m_l$. A motif $m_i$, maximal in composition, is also maximal in length if and only if there exists no motif $m_j$, $j \neq i$, such that $m_i$ is a sub-motif of $m_j$ and $|L_{mi}|=|L_{mj}|$. A maximal motif is maximal both in composition and in length.

Cell: Given s, a cell is the smallest substring in any pattern on s, that has exactly two solid characters: one at the start and the other at the end position of this substring.

$m^s_1 \succ m^s_2$: Given two cell $m^s_1$ and $m^s_2$, $m^s_1 \succ$ if one of the following holds:
1. $m^s_1$ has only solid characters and $m^s_2$ has at least one non-solid character
2. $m^s_2$ has the "–" character and $m^s_1$ does not
3. $m^s_1$ and $m^s_2$ have $d_1, d_2 > 0$ dot characters respectively and $d_1 < d_2$.

Clearly, the above defines a partial order on the cells.

$\odot$-compatible, $m_l \odot m_2$: $m_l$ is $\odot$-compatible with $m_2$ if the last solid character of $m_l$ is the same as the first solid character of $m_2$. Further if ml is $\odot$-compatible with $m_2$, then $m=m_l \odot m_2$ is the concatenation of $m_l$ and $m_2$ with an overlap at the common end and start character and $$L'_m=\{((x,y),z)|(x,l),z)\in L'_{m1},((l,y),z)\in L'_{m2}$$

For example if $m_l$=ab and $m_2$=b.d then $m_1$ is $\odot$-compatible with $m_2$ and $m_l \odot m_2$=ab.d. However, $m_2$ is not $\odot$-compatible with $m_l$.

Fixed vs. Variable Spacers

We now discuss two different kinds of spacers, fixed and variable. Given a constant D, for rigid motifs it is to be interpreted that the motif can have fixed 1 or 2 or ... or D dots between successive solid characters and for extensible motifs can have between 1 to D dot characters between successive solid characters. Also, let R be the set of all rigid maximal motifs and let $\epsilon$ be the set of all extensible motifs. The following statement can be easily verified. Given a string s with parameters k and D, then if $m_r \in R$, then there must be $m_f \in \epsilon$ such that either $m_r=m_f$ or $m_r$ is a substring of $m_f$.

Consider the following two examples. Example 1: If s=aycazxc with k=2, D=2, then $\epsilon=\{a-c\}$ and R={ } with $|\epsilon|>|R|$. Example 2: Let s=abycpqdefabzcxdef with k=2, D=2. Then R={ab.c, de f} and $\epsilon=\{ab.c-def\}$ with $|R|>|\epsilon|$. Thus, although in theory there is no relationship between |R| and $>|\epsilon|$, in practice $|R|<|\epsilon|$.

Inexact Suffix Tree

We introduce a data structure representing a string, called an inexact suffix tree that efficiently stores all the suffixes of maximal patterns with wild cards (variable or don't-care tokens). The suffix is inexact in the sense that it contains wild cards.

Referring to FIG. 1, there is shown an inexact suffix tree for a string s=axcdabyday and with D=2. A solid circle denotes a leaf node. The root node is labeled Z and the internal nodes are labeled A through I. The unique path from the root node (Z) to the leaf node labeled by integer i, represents a string $p \preceq s[i \ldots n]$.

The inexact suffix tree is built as follows: Given a string s of size n, let $\$ \notin \Sigma$. We terminate s with $ as s$. Let D be the maximum number of don't care characters between any two consecutive solid characters and let k be the minimum number of times a extensible pattern must occur. Consider a rooted tree T with edges labeled by non empty strings with the following properties:

Each leaf node is labeled by an integer $1 \leq l \leq n$. The edge label is a sequence on $\Sigma+\{`.`,`-`\}$. All the outgoing edges of the root node are labeled by strings that start with a solid character. No two edges out of a node can be labeled with strings that start at the same solid character. Each edge label can have at most D consecutive '.' character and at most one consecutive '.' character. Also, the last character must be solid. For an internal node i, let R(i) be the set of integer labels of the leaves reachable from i.
(a) |R(i)|>1 for all i.
(b) For any two immediate successor internal nodes $j_1$ and $j_2$ of i, $R(j_1) \neq R(j_2)$.
(c) Consider an internal node i and its immediate successor j and let $p = x_1 x_2 \ldots x_J$, where $x_i \notin \Sigma$ or $x_i$ is the don't-care or '–' character, be the label on edge from i to j.
  i. $R_j \subset R_i$.
  ii. Consider all possible labels $p_1, p_2, \ldots p_l$ satisfying the constraint 2 above with each having J characters and the same $R_j$, then $p_1, p_2, \ldots p_l \preceq p$.
  iii. There does not exist label p' satisfying all the constraints above with p' having less than J characters and a possible successor node j' of i such that $R_j \subset R_{j'}$, and $|R_{j'}|>1$.

It is easy to now see that given D, the inexact suffix tree is well defined and is unique. When D=0, τ is also called a suffix tree of s. The tree described above is for k=2 for clarity of exposition. It can be trivially generalized to k>2.

The unique path from the root node to the leaf node labeled by integer i, represents s[i . . . n] that is obtained by traversing from the root node to the leaf node: concatenating the edge labels of this path gives p and $p \preceq s[i \ldots n]$.

The string associated with the internal node E is p=a..da.y obtained by concatenating the labels on the edges from the root node Z. Given strings $p_i$, $1 \leq i \leq l$, their meet is p if and only if $p \preceq p_i$, and there exists no p' such that $p \preceq p' \preceq p_i$, for all i. We make the following observations about the inexact suffix tree described above. The string obtained by concatenating the edge labels on the unique path from the root to an internal node corresponds to a suffix of a maximal extensible pattern with parameter D and k=2.

Equivalently, consider the internal node j and let p be the string obtained by concatenating the labels on the edges in the path from the root node to the node j. Then p is the meet of the suffixes s[i . . . n] where i∈R(j).

The inexact-suffix tree not only suggests a way of detecting all the extensible patterns efficiently but also gives a data structure for storing the extensible patterns for efficient retrieval or matching.

Implementation

An inexact suffix tree is constructed implicitly (in a different order) in an implementation that is discussed herein. Notice that the suffix tree, described above and illustrated in FIG. 1, produces all the suffixes of the maximal motifs. In the implementation, we detect the suffixes as early in the process as possible and discard them.

Figure 2A:
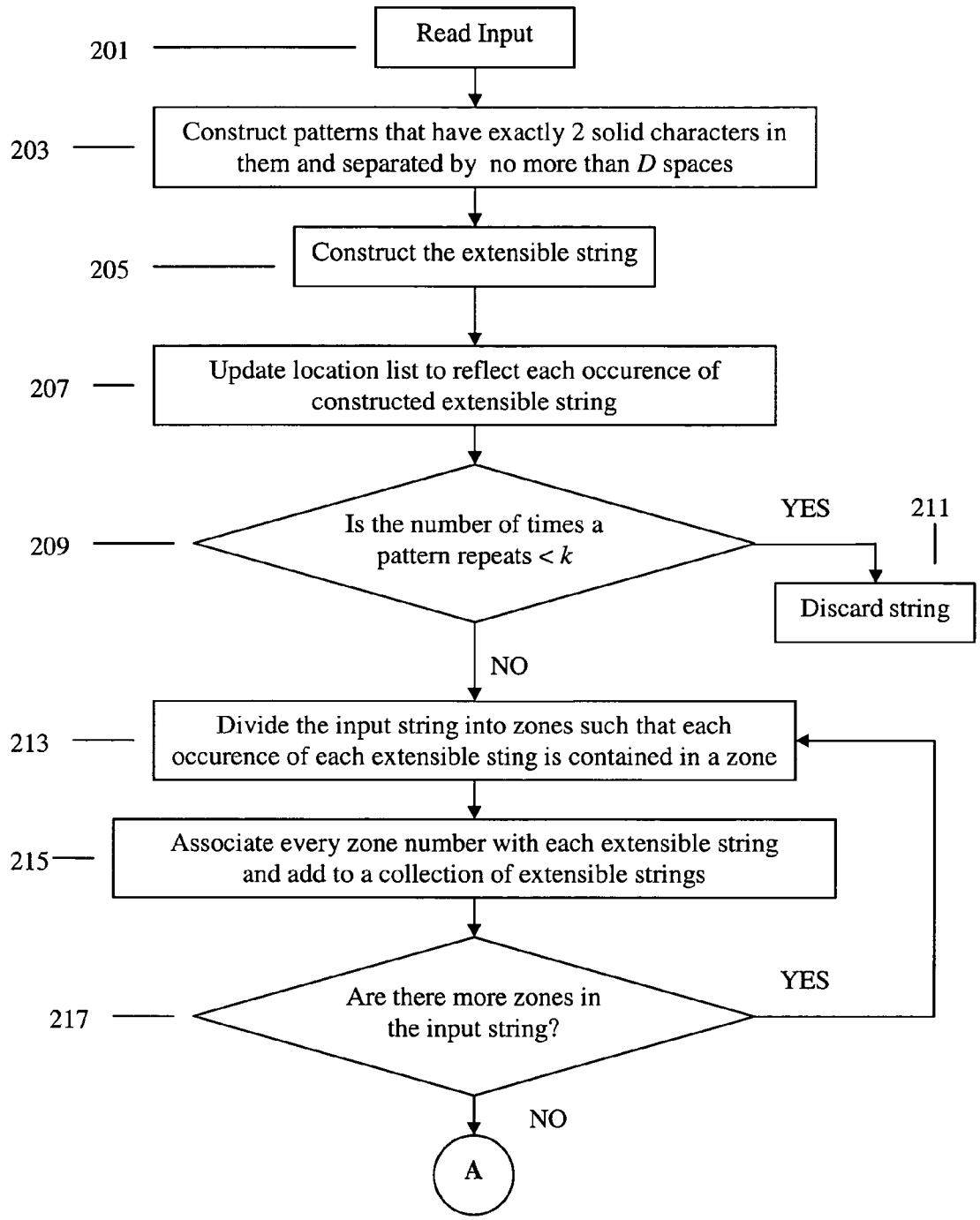
FIGS. 2*a–e* are a flow chart illustrating a method according to the invention.

Referring to FIG. 2a, in step 201 we receive an input of a string s of size n and two positive integers, k and D. We begin with a few definitions that will be used in this step. Notice that a cell is the smallest extensible component of a maximal pattern and the string can be viewed as a sequence of overlapping cells. If no don't care characters are allowed in the motifs then the cells are non-overlapping.

The algorithm comprises the following steps:

In step 203 of FIG. 2a, we begin by constructing patterns that have exactly two solid characters in them and separated by no more than D spaces or "." characters. This can be done by scanning the string s from left to right. Further, for each location we store start and end positions of the pattern. In the following example a character could also be referred to as a cell, and a string of characters can also be referred to as cells.

For example, if s=abzdabyxd and k=2, D=2, then all the patterns generated at this step are: ab, a.z, a..d, bz, b.d, b..a, zd, z.a, z..b, da, d.b, d..y, a.y, a..x, by, b.x, b..d, yx, y.d, xd, each with a list of where they occur. Further $L_{ab}=\{(1, 2), (5, 6)\}$, $L_{a.z}=\{(1, 3)\}$ and so on.

In the next step 205, we construct the extensible cells by combining all the characters with at least one dot character and the same start and end solid characters. In step 207 we update the location list to reflect the start and end position of each occurrence. In the previous example, we generate b–d at this step with $L_{b-d}=\{(2, 4), (6, 9)\}$.

In decision 209, we determine whether the number of times a pattern repeats is less than k. Next in step 211, if $|L_m|<k$, then we discard all extensible strings m. Continuing the previous example, the only surviving cells are ab, b–d with the following equation:

$$L_{ab}=\{(1,2),(5,6)\} \text{ and } L_{b-d}=\{(2,4),(6,9)\}$$

This step is used only for quick comparison of location lists and is not vital for the working of the algorithm. Nevertheless, in practice it is a time saving step in detecting non maximal motifs (suffixes of maximal motifs).

In step 213 the input sequence s is broken up into $1 \geq 1$ subsequences, called zones, $Z_1=s[1, j_1], Z_2=s[j_1+1, j2] \ldots, Z_l=s[j_{l-1}+1, j1] Z_{l+1}=s[j_1+1, |s|]$ such that each occurrence of each cell is fully contained in a subsequence. This works best when 1 is much smaller than n.

We now continue the previous example, l=1 with $z_1=4$. Thus $Z_1$=abzd and $Z_2$=abxyd. In step 215 we associate the zone number with every occurrence of the cell, and add each occurrence to a collection of cells B, this is continued as step 217 checks all the subsequences of the input sequence have been associated with zones. Thus the augmented location lists are $$L'_{ab}=\{((1, 2),1),((5, 6),2)\} \text{ and } L'_{b-d}=\{((2,4),1),((6,9), 2)\}$$

We make the following statements about the zones that is straightforward to verify.

Given s, if an occurrence of a cell $m_i^s$ contained in a zone $Z_i$, then the occurrence of a corresponding maximal extensible pattern $m_i$ that contains this occurrence of $m_i^s$ is also contained in $Z_i$. Hence, the corresponding occurrence of every nonmaximal extensible pattern w.r.t $m_i$ is also contained in $Z_i$.

Consider a maximal extensible motif $m_i$ with $|L_{mi}|=K$. Let the K-tuple of $m_i$ of only the zone numbers be defined as $Z_{mi}=(z_1, z_2, \ldots, z_k)$ Then for every nonmaximal motif m'$_i$ w.r.t. $m_i$ the following holds: $Z_{m'i}=Z_{mi}$.

Iteration Phase

We begin with a few definitions that will be used in these steps which are used in an iteration function described below. Let B be a collection of extensible strings. If m=Extract (B), then m∈B and there does not exist m'∈B such that m'≻m holds.

The iteration function will have an input of a collection of extensible strings B and an extensible string m'extracted from the collection of extensible strings B and an output of maximal extensible patterns. The output of maximal extensible patterns will be added to a collection of maximal extensible patterns called Result. The following definition is a reiteration of the order of the nodes described in constructing the inexact suffix tree, but stated in terms of cells for clarity of exposition.

The procedure is best described by the following pseudocode.

| | |
|---|---|
| Result ←{ }; | Iterate(m,B,Result) |
| B←{$m^s_1$ \| $m^s_1$ is a cell}; | { |
| | G:1   m'←m; |
| For each m = Extract(B) | G:2   For each b = Extract(B) with |
| Iterate(m,B,Result); | G:3     ((b⊙-compatible m') OR |
| |        (b ⊙-compatible b)) |
| Result ←Result ∪ B | G:4     If (m' ⊙-compatible b) |
| | G:5         mt ←m '⊙ b; |
| | G:6         If siblingInconsistent ($m_t$) exit; |
| | G:7         If ( \| $L_{m'}$ \| = \| $L_b$ \| ) B←B – {b}; |
| | G:8         If ( \| $L_{m'}$ \| ≧ k) m' ←$m_t$ |
| | G:9     If (b ⊙ compatible m') |
| | G:10        $m_t$ ←b ⊙ m' |
| | G:11        If SiblingInconsistent($m_t$) exit; |
| | G:12        If ( \| $L_{m'}$ \| = \| $L_b$ \| ) B←B – {b}; |
| | G:13        If ( \| $L_{m'}$ \| ≧ k) m' ←$m_t$ |
| | G:14     Iterate (m',B,Result) |
| | G:15     For each r ∈ Result with $Z_r$ = $Z_{m'}$ |
| | G:16        If (m' is not maximal w.r.t. r) |
| |            return; |
| | G:17     Result ←Result ∪ {m'}; |
| | } |

Steps G:15–16 detect the suffix motifs of already detected maximal motifs. Result is the collection of all the maximal extensible patterns.

Figure 2B:
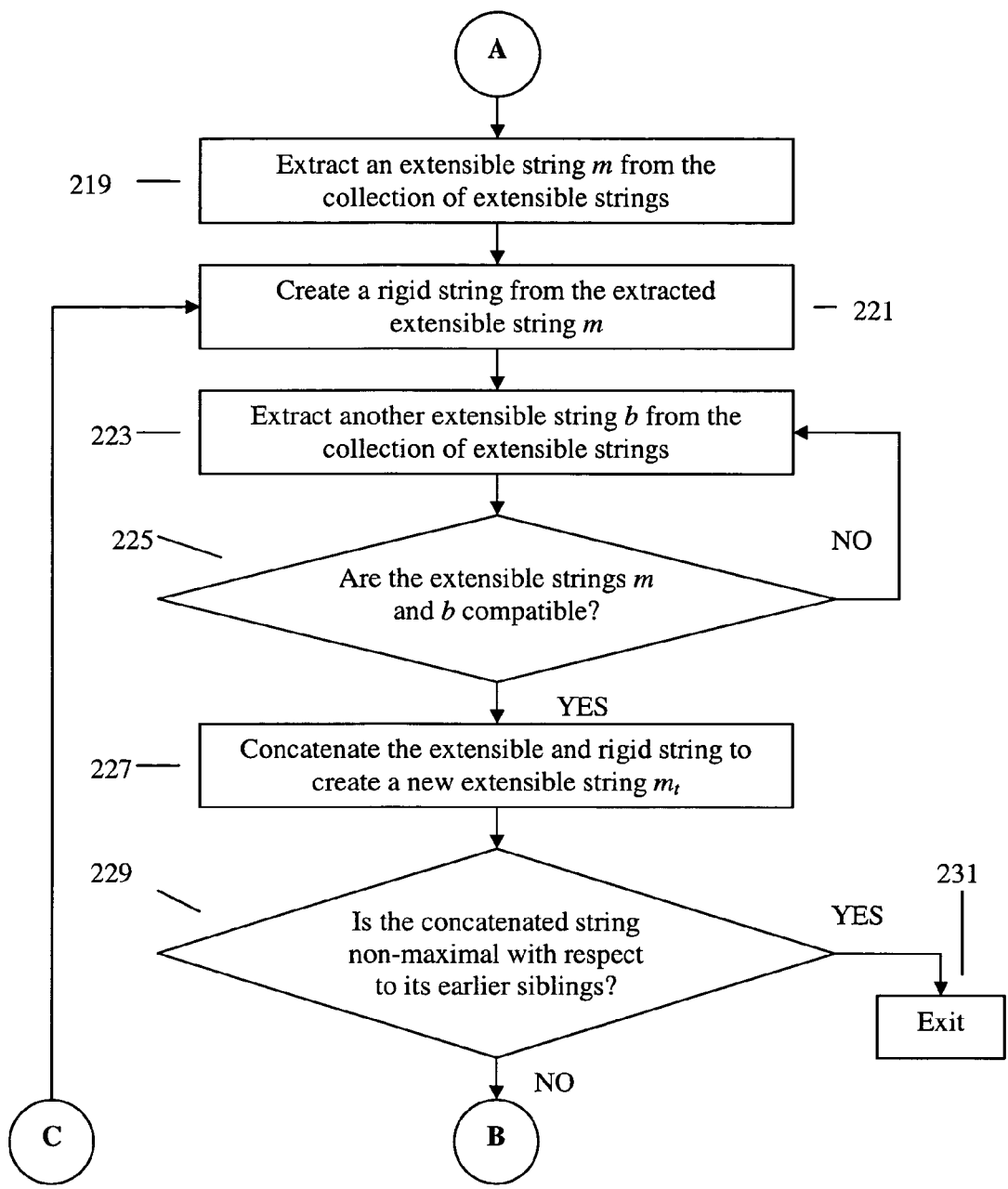

Referring to FIG. 2*b*, in step 219 we extract an extensible string m from a collection of extensible strings B.

In the next step 221, we create a rigid string m' from the extracted extensible string m.

In the next step 223, we extract another extensible string b from the collection of extensible strings B.

Next in step 225, we determine whether the rigid string m' is compatible with the extensible string b, or if the extensible string b is compatible with the rigid string m'. If it is determined that they are not compatible with each other, then we replace the extensible string b with another extensible string extracted from the collection of extensible strings B.

In step 227, if both the rigid string m' and the extensible string b are compatible with each other, then they are concatenated to form a new extensible string $m_t$.

In step 229, we then check if the concatenated extensible string $m_t$ is non-maximal with respect to its earlier siblings by checking the location lists. This routine corresponds to backtracking, which is always only when the sibling has don't care characters in it.

In step 231, if the concatenated string $m_t$ is non maximal, then the method exits to the next iteration (exits the loop).

Figure 2C:
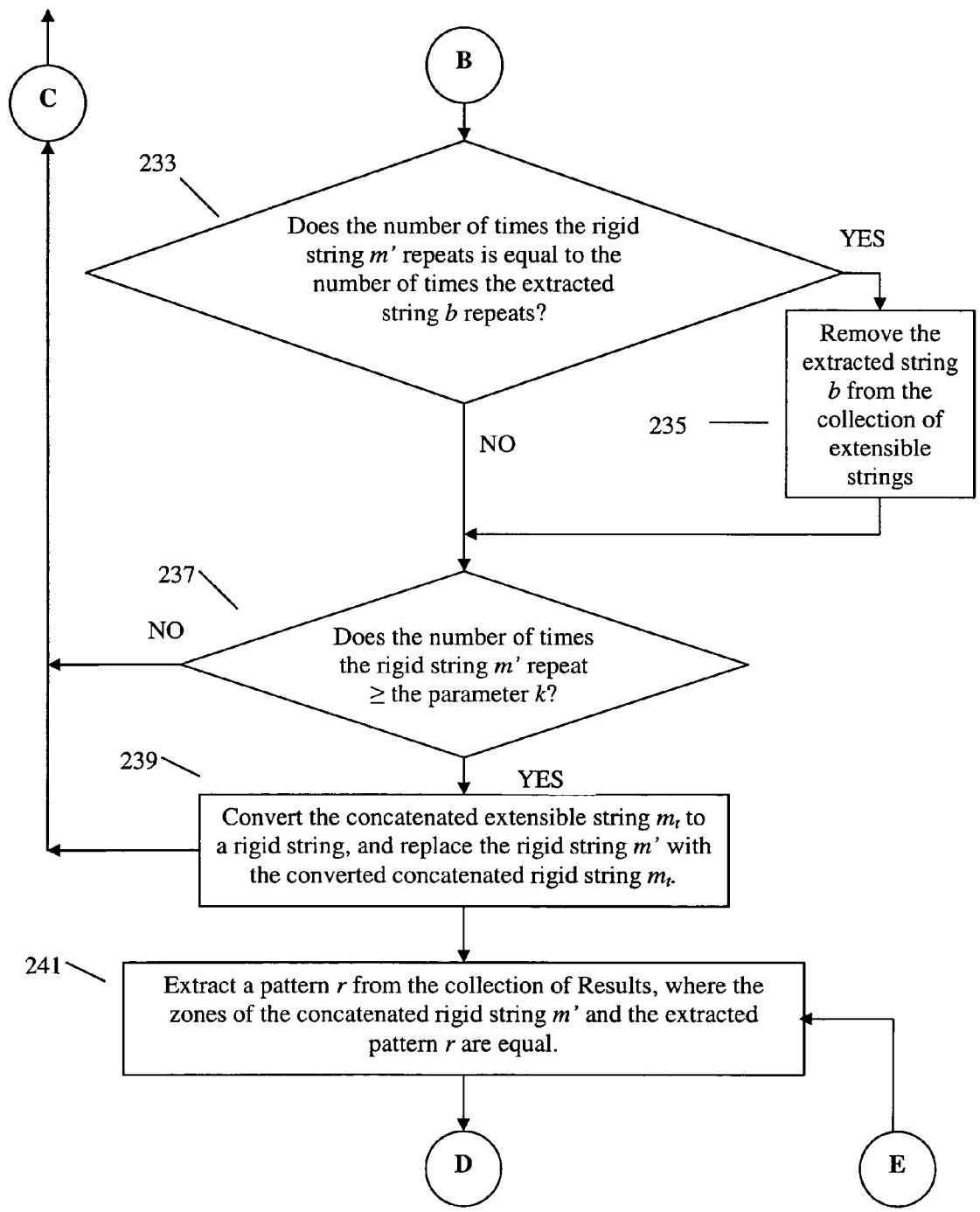

Referring to FIG. 2*c* in step 233, if the concatenated string extensible string $m_t$, is maximal with respect to its siblings, then we check if the number of times the rigid string m' repeats is equal to the number of times the extracted string b repeats.

In step 235 if the number of times the rigid string m' repeats is equal to the number of times the extracted string b repeats is true, then we remove the extracted string b from the collection of extensible strings B.

In step 237 if the number of times the rigid string m' repeats is equal to the number of times the extracted string b repeats is false, or after we remove the extracted string b from the collection of extensible strings, we determine if the number of times the rigid string m' repeats is greater than or equal to the parameter value k.

If the number of times the rigid string m' repeats is not greater than or equal to the parameter value k, the method returns to step 233 and repeats the iteration.

In step 239 if the number of times the rigid string m' repeats is greater than or equal to the parameter value k, then we convert the concatenated extensible string $m_t$ to a rigid string and replace the rigid string m' with the converted concatenated string $m_t$. The iteration function in G:14 repeats recursively until collection of cells B is empty. Result is the collection of all the concatenated strings extracted. Result is updated whenever a non-maximal pattern is found.

In step 241 we continue to function G:15 when we cannot find any more strings b to concatenate with m.

Figure 2D:
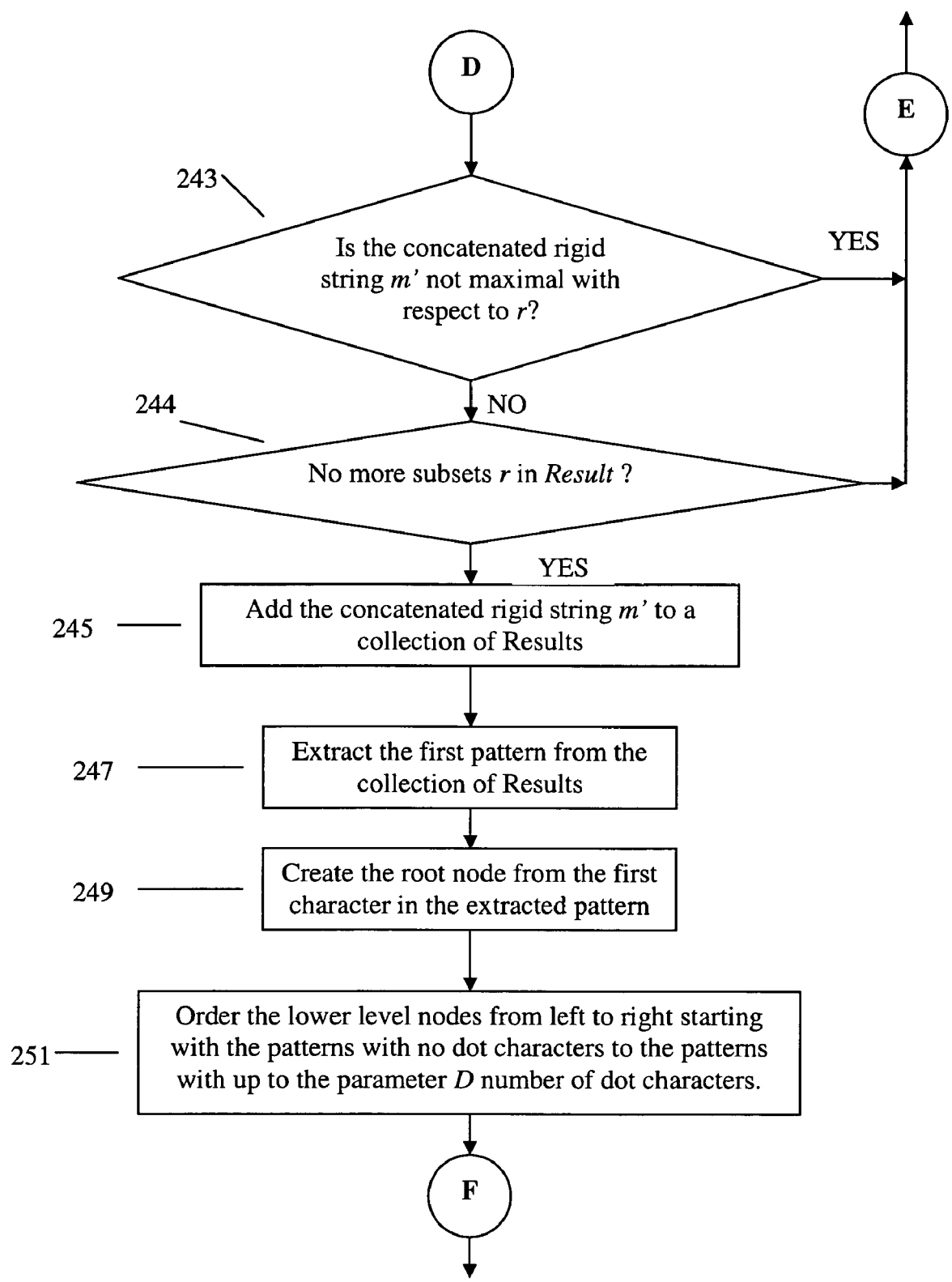

Referring to FIG. 2*d* step 243, determine if the concatenated rigid string m' is not maximal with respect to the extracted pattern r.

If the concatenated rigid string m' is not maximal with respect to the extracted pattern r, then we return to G:15.

In step 244 we determine if there are any remaining patterns r in the collection of results Results to extract.

In step 245 if there are no remaining patterns r in the collection of results Results, then we add the concatenated rigid string m' to the collection of results Results.

If there are remaining patterns in the collection of results Results, then continue to extract from the collection of results Results by returning to step 241. Once the iteration function has completed, we continue by constructing an inexact tree from the collection of results Results.

In step 247 we begin by extracting the first pattern from the collection of results.

In step 249 we create a root node from the first character in the extracted pattern.

Figure 3:
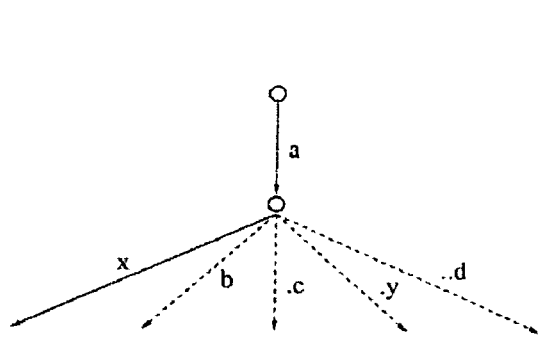
FIGS. 3–14 illustrate construction of an inexact suffix tree for a string comprising the character sequence axcdabydaxy.

Next, in step 251, we then continue by ordering lower level nodes from left to right of the root node starting with the patterns with no dot characters on the left, to the patterns with up to the parameter D number of dot characters. This step generates a tree with a single lower level, as shown in FIG. 3.

Figure 2E:
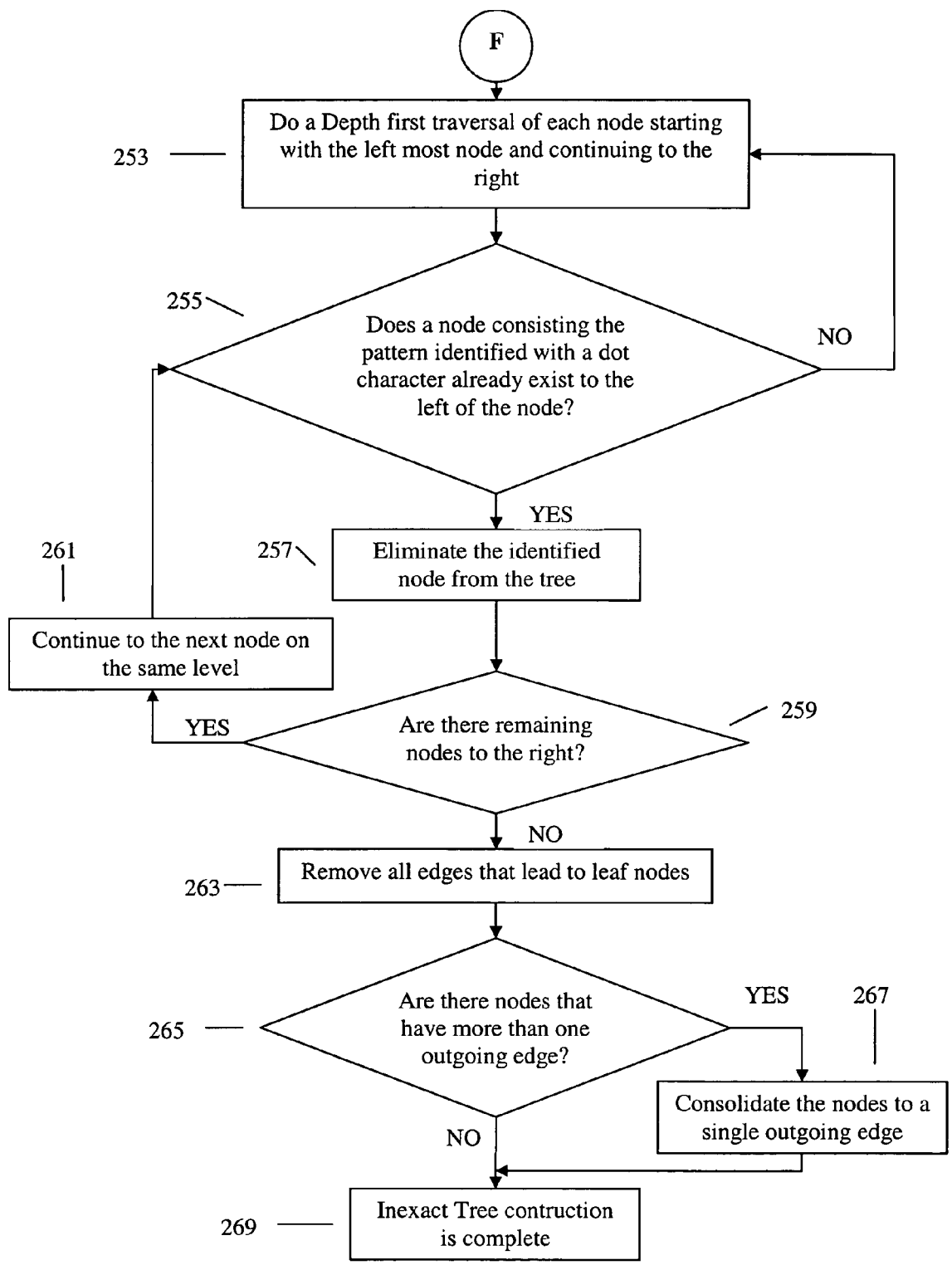
Figure 4:
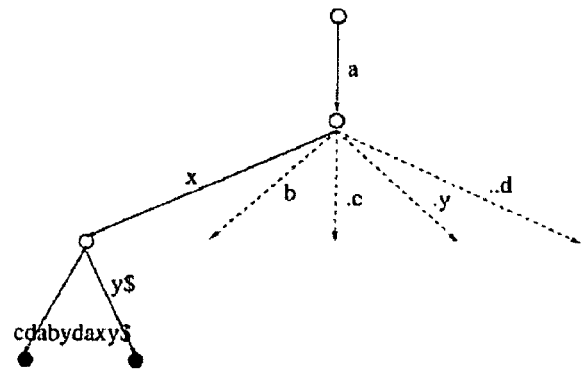
Figure 5:
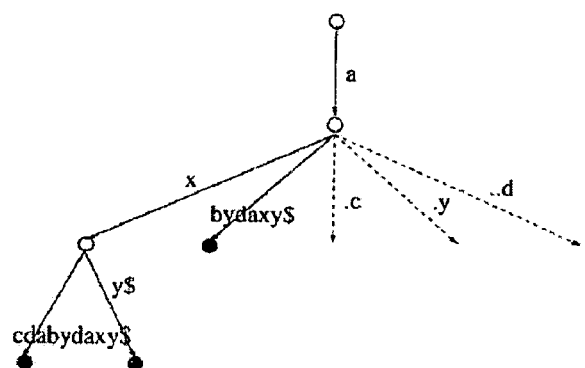

In step 253 of FIG. 2*e*, then perform a depth first traversal of each node starting with the left most node and continuing to the right. This step is illustrated in FIG. 4 for the first node on the left and continues as shown in FIG. 5 with the next node to the right.

Figure 6:
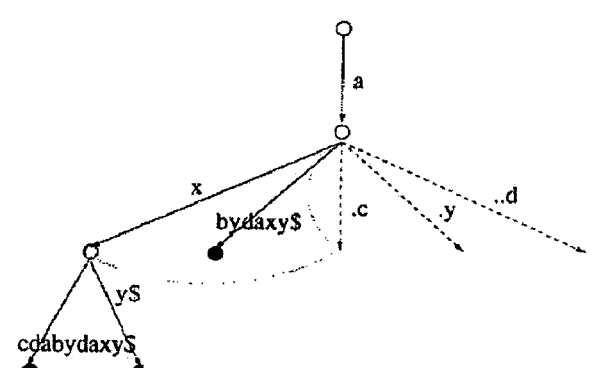

The tree construction involves some limited backtracking. In step 255, the backtracking is always only one level deep and it occurs when the edge label has don't care characters in it. For example if the edge label is ".a", then the other siblings of this node are examined to see if the don't-care character is required. This step is illustrated in FIG. 6.

Figure 7:
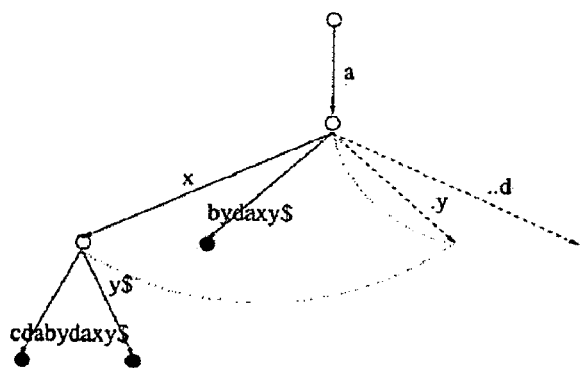
Figure 8:
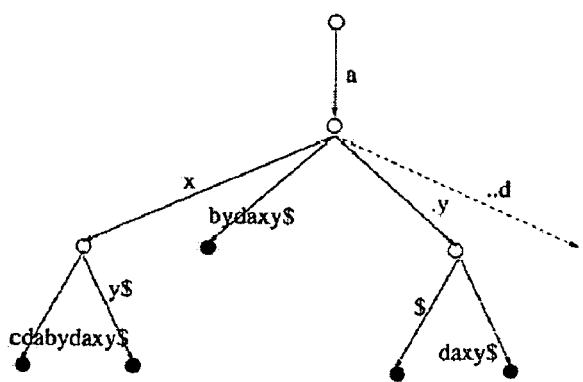
Figure 9:
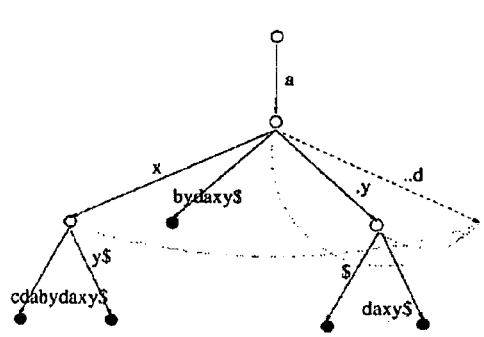
Figure 10:
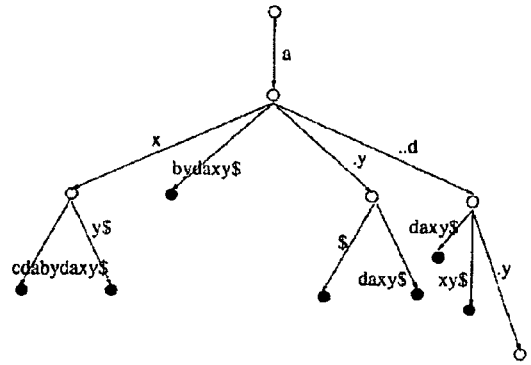

In step 257 we eliminate the identified node from the tree if the backtracking identifies an edge to the left which already contains the pattern. Otherwise we keep the node and perform a depth first traversal as in step 253 as shown in FIG. 7 and FIG. 8. FIG. 9 and FIG. 10 also show a node that does not get eliminated because of sibling inconsistencies.

Figure 11:
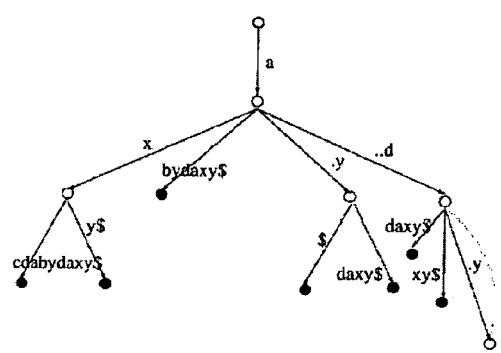
Figure 12:
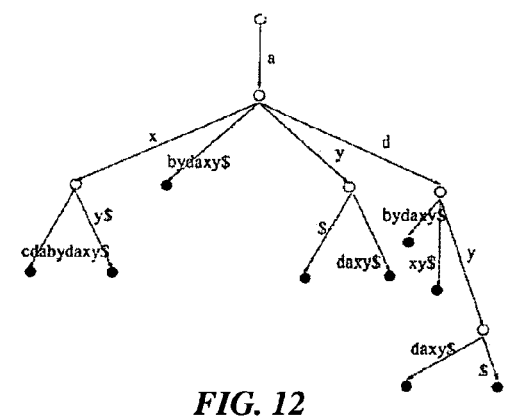

Step 259 determines if there are any remaining nodes to be checked for inconsistencies. If so, then we continue to step 261, which checks the next node to the right. If there are no further nodes that need to be checked we continue to step 263, which removes all edges that lead to leaf nodes, which is shown in FIG. 11.

Figure 13:
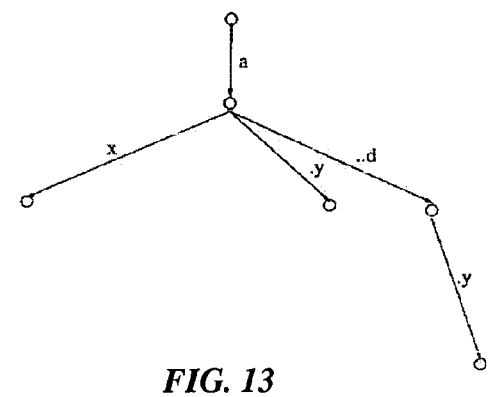

Step 265 checks if there are nodes remaining that have more than one outgoing edge. FIG. 13 shows the rightmost node has an outgoing edge.

Figure 14:
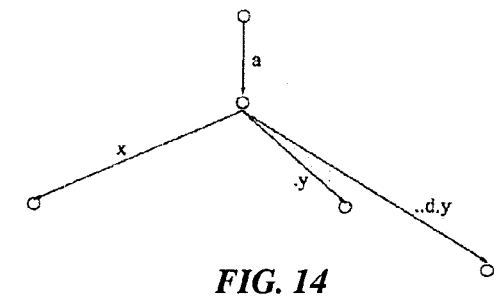

In step 267 if there are nodes with more than one outgoing edge then the outgoing edge is consolidated to a single outgoing edge, as shown in FIG. 14.

Step 269 completes the construction of the inexact suffix tree. FIG. 14 is a complete inexact suffix tree.

Allowing motifs to have a variable number of gaps (or don't-care characters), i.e., patterns with spacers or extensible motifs, considerably increases the expressibility of the motifs. It is likely that some information missed by rigid motifs is captured by the extensible motifs. The invention is an implementation of an extensible motif discovery algorithm that guarantees the detection of every extensible pattern. One of the directions being currently investigated is to use the method according to the invention to detect extensible patterns in an unsupervised manner on protein sequence databases, and then use suitable pruning techniques to compare the detected patterns with known motifs.

Referring to FIG. 15, there is shown a table showing the output of a small sample, wherein the input data is a collection of fibronectin sequences with D=7 and k=2. The first column gives the number of occurrences of the motif shown in the third column; the second column gives the number of distinct sequences in which the motif appears and the last column gives the occurrence in the format (s: $i_1$ $i_2$), where s is the sequence number and the motif starts at $i_1$ ending at $i_2$.

Referring to FIG. 16, there is shown a table wherein the input data is a collection of fibronectin sequences with D=7 and k=2. A small sample output is shown in the table. The first column gives the number of occurrences of the motif shown in the third column; the second column gives the number of distinct sequences in which the motif appears. This version uses homologous grouping of the amino acid bases shown in square brackets. The occurrence lists have been removed to avoid clutter.

Referring to FIG. 17, there is shown a table wherein for a small sample output, the input data is a collection of fibronectin sequences with D=7 and k=2. Here the gaps are annotated: $-(i_1, i_2)$, which indicates that the number of gaps are between $i_1$ and $i_2$ in the occurrences in the input.

Figure 18:
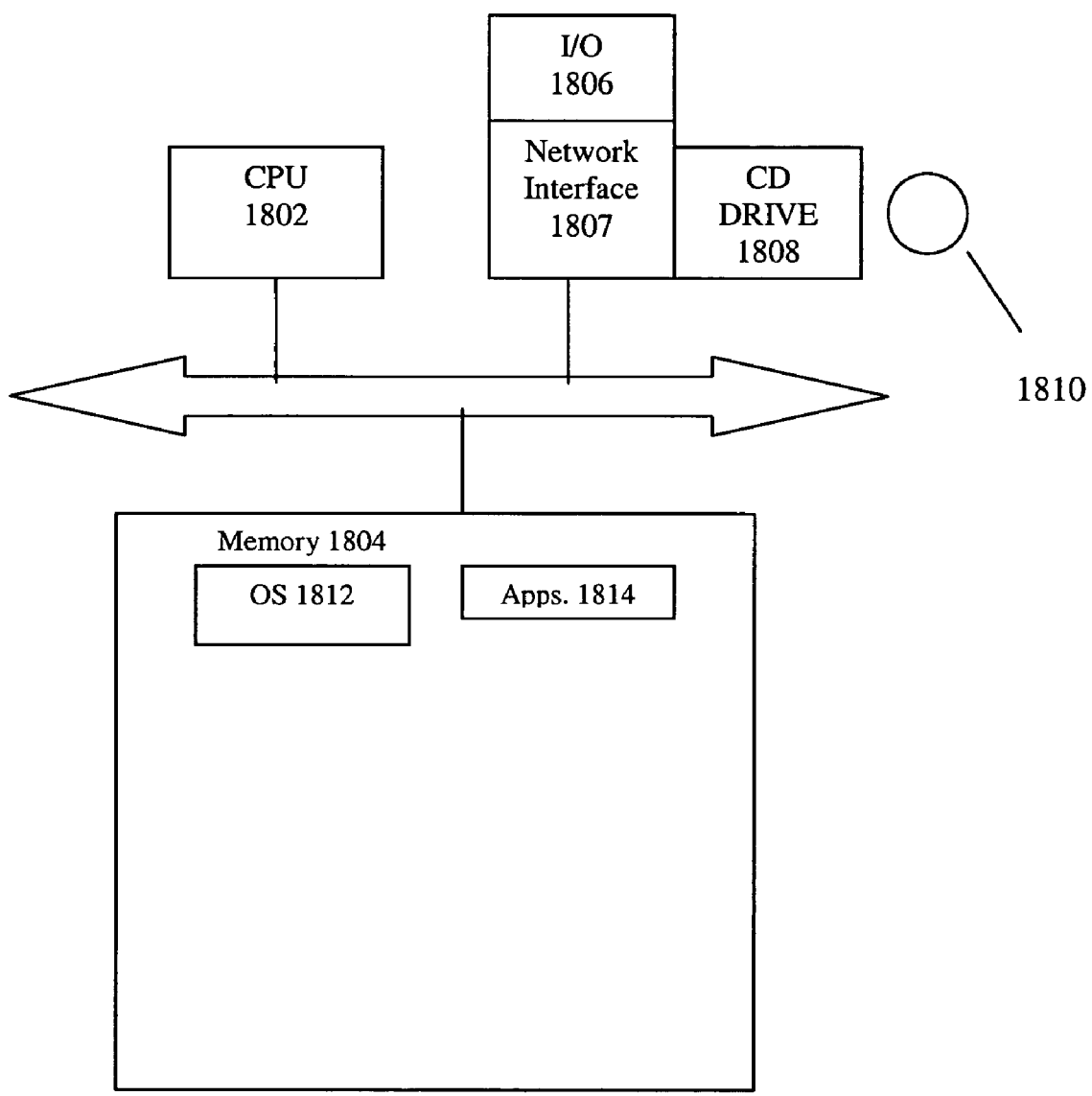
FIG. 18 is a block diagram of an information processing system using the invention.

The system of FIG. 18 is useful on primarily biological data such as DNA and protein sequences. However the generality of the system makes it equally applicable in other data mining, clustering, and knowledge extraction applications. The system comprises an input/output device 1806, a CD Drive 1808, a central processing unit 1802, and a memory unit 1804. The memory unit 1804 further comprises an operating system 1812, and an application 1814. The input/output device further comprises a network interface 1807.

Therefore, while there has been described what is presently considered to be the preferred embodiment, it will be understood by those skilled in the art that other modifications can be made within the spirit of the invention.

What is claimed is:

1. A method for determining patterns in an input string of tokens, comprising steps of:
   identifying extensible patterns in the input string;
   creating an inexact tree for the input string, using the patterns identified; and
   displaying a set of extensible patterns identified by the inexact tree; wherein creating the inexact tree comprises creating nodes and edges, connecting the nodes, wherein each node represents a subset of a string and each edge connects a lower order node to a higher order node; wherein each subset comprises a pattern comprising extensible string; and wherein each extensible string comprises at least one dot token.

2. The method of claim 1, further comprising receiving a parameter k specifying the minimum times an extensible pattern must occur in a sequence.

3. The method of claim 1, wherein the step of identifying patterns in the input string B comprises creating a rigid string m' from an extensible string m.

4. The method of claim 1 wherein the step of identifying patterns in the input string B comprises extracting a subset of tokens b from the input string B.

5. The method of claim 4 analyzing the subset of tokens b to determine whether the subset is compatible with the rigid string m'.

6. The method of claim 5 wherein if the subset b is compatible with the rigid string m' the subset and the rigid string are concatenated into a new rigid string $m_r$.

7. The method of claim 6 further comprising the step of running a routine for determining whether the concatenated string is non maximal with respect to nodes of the same order in the tree.

8. The method of claim 7 further comprising removing each node from the tree that is non maximal with respect to nodes of the same order in the tree.

9. The method of claim 8 wherein if the magnitude of the location list of the rigid string m' is equal to the magnitude of the location list of the subset of tokens b then the size of the collection of tokens B is reduced by removing the subset of tokens b determined in the step of extracting a subset of tokens from the input string.

10. The method of claim 9 wherein if the number of times the rigid string pattern repeats is greater than the minimum number of times an extensible pattern must occur in a sequence k, then the concatenated extensible string $m_t$ is converted into a rigid string m'.

11. The method of claim 10 wherein said method is performed on the converted rigid string m'.

12. The method of claim 11 further comprising identifying a zone for each subsequence of tokens $Z_r$ such that each occurrence of each pattern is fully contained within the zone of the rigid string $Z_{m'}$.

13. The method of claim 11 further comprising determining whether the rigid string m' is not maximal with respect to a string of tokens r that are returned from the determination of the routine.

14. The method of claim 13 wherein the result of the routine m' is added to a collection of maximal extensible patterns Result.

15. A system comprising:
   an input/output device for receiving information including an input string; and
   a processor for identifying extensible patterns;
   identifying extensible patterns in the input string;
   creating an inexact tree for the input string, using the patterns identified; and
   displaying a set of extensible patterns identified by the inexact tree; wherein creating the inexact tree comprises creating nodes and edges, connecting the nodes, wherein each node represents a subset of a string and each edge connects a lower order node to a higher order node; wherein each subset comprises a pattern comprising extensible string; and wherein each extensible string comprises at least one dot token; and
   a memory for storing identified patterns and for storing the inexact suffix tree.

16. The system of claim 15 wherein the input/output device further comprises a CD ROM drive.

17. The system of claim 15 wherein the input/output device further comprises a network interface.

18. The system of claim 15 wherein the memory further comprises an operating system.

19. The system of claim 15 wherein the memory further comprises an application.

20. A computer readable medium for determining patterns in an input string of tokens, comprising instructions for:

identifying extensible patterns in the input string; creating an inexact tree for the input string, using the patterns identified; and displaying a set of extensible patterns identified by the inexact tree; wherein creating the inexact tree comprises creating nodes and edges, connecting the nodes, wherein each node represents a subset of a string and each edge connects a lower order node to a higher order node; wherein each subset comprises a pattern comprising extensible string; and wherein, each extensible string comprises at least one dot token.

* * * * *